United States Patent

Peglion et al.

[11] Patent Number: 5,968,954
[45] Date of Patent: Oct. 19, 1999

[54] 2-AMINOINDAN COMPOUNDS AS $5HT_{1B}$ ANTAGONISTS

[75] Inventors: Jean-Louis Peglion, Le Vesinet; Bertrand Goument, Viroflay; Mark Millan, Le Pecq; Alain Gobert, Saint Denis, all of France

[73] Assignee: Adir et Compagnie, Courbevoie, France

[21] Appl. No.: 09/031,490

[22] Filed: Feb. 26, 1998

[30] Foreign Application Priority Data

Feb. 27, 1997 [FR] France .................................. 97.02360

[51] Int. Cl.⁶ ...................... A61K 31/445; C07D 405/12
[52] U.S. Cl. ................... 514/321; 514/318; 514/319; 514/324; 514/422; 546/115; 546/193; 546/196; 546/197; 546/202; 546/204; 546/205; 548/525; 548/526; 548/527
[58] Field of Search ..................... 546/193, 196, 546/197, 202, 204, 205, 115; 514/318, 319, 321, 324, 422; 548/525, 526, 527

[56] References Cited

U.S. PATENT DOCUMENTS 5,767,116  6/1998  Kerrigan et al. .................. 514/212

*Primary Examiner*—Ceila Chang
*Attorney, Agent, or Firm*—The Firm of Gordon W. Hueschen

[57] ABSTRACT

New 2-aminoindan compounds of formula:

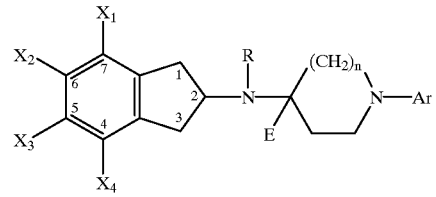

wherein: n, Ar, R, E, $X_1$, $X_2$, $X_3$, and $X_4$ are as defined in the description, in the form of a racemic mixture and in the form of optical isomers, and physiologically-tolerable acid addition salts thereof. The products of the invention are useful as medicaments and exhibit selective binding affinity for the $5HT_{1B}$ receptors.

21 Claims, No Drawings

2-AMINOINDAN COMPOUNDS AS 5HT$_{1B}$ ANTAGONISTS

The present invention relates to new 2-aminoindan compounds. It relates more especially to compounds of formula I:

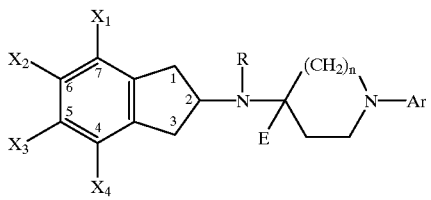

wherein:

n represents 1 or 2;

- Ar represents:

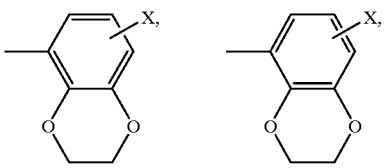

(X being a hydrogen or flourine atom)

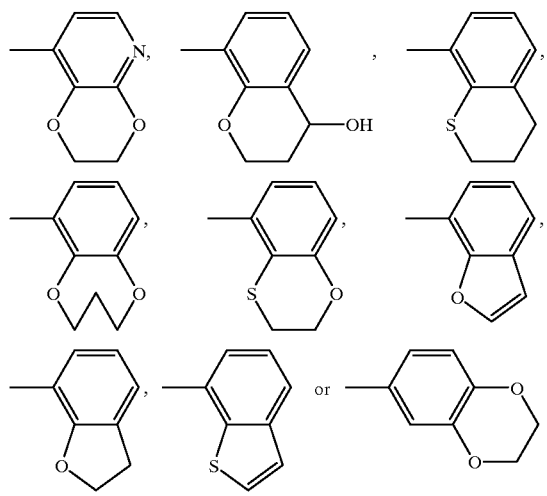

R represents a hydrogen atom, a linear or branched (C$_1$–C$_5$)-alkyl radical or an aralkyl radical, E represents a hydrogen atom or a methyl radical, and X$_1$, X$_2$, X$_3$ and X$_4$, which may be identical or different, each represents a hydrogen or halogen atom, a straight-chain or branched (C$_1$–C$_5$)-alkyl or (C$_1$–C$_5$)-alkoxy radical, a trifluoromethyl, hydroxy, cyano or nitro radical, or a radical

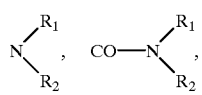

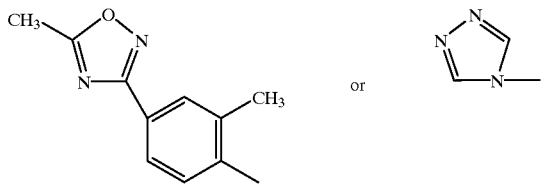

wherein: R$_1$, R$_2$ and R$_3$, which may be identical or different, each represents a hydrogen atom or a straight-chain or branched (C$_1$–C$_5$)-alkyl radical, and R$_4$ represents a straight-chain or branched (C$_1$–C$_5$)-alkyl radical, and/or a pair adjacent to one another form, together with the carbon atoms of the phenyl nucleus to which they are bonded, a 5-membered or 6-membered ring composed of atoms selected from the atoms carbon, oxygen, nitrogen and sulphur, where they exist in the form of a racemic mixture or in the form of optical isomers, and physiologically tolerable acid addition salts thereof The products of the present invention may be used as medicaments in the treatment of disorders in which involvement of the serotoninergic system has been demonstrated, such as psychiatric disorders (depression, anxiety, panic attack, schizophrenia, aggression, impulsive disorders, obsessive-compulsive disorders), degenerative diseases (Parkinson's disease, Alzheimer's disease), pain, migraine, headaches, cerebral vascular accidents, bulimia, anorexia, drug abuse and also in cardiovascular disorders (unstable angina) since, like the central nervous system, the serotoninergic system is also present in the cardiovascular areas. Numerous serotonin receptors have been identified and recently have been cloned. They have been classified into seven major classes, 5HT$_1$ to 5HT$_7$, on the basis of their primary structure and their mode of coupling with the transduction systems (cf. F. G. Boess, Molecular Biology of 5HT Receptors, Neuropharmacol., 1994, 33, 275). Those classes are themselves divided into sub-types. Sub-types 5HT$_{1A}$, 5HT$_{1B}$ (formerly 5HT$_{1D\beta}$) and 5HT$_{1D}$ (formerly 5HT$_{1D\alpha}$) are known for the 5HT$_1$ receptor (for a recent review and discussion of the nomenclature see R. P. Hartig, Trends in Pharmacol. Sciences, 1996, 17 103).

The application of the present invention concerns more especially the 5HT$_{1B}$ receptor since the products of the invention act as powerful and selective ligands of that receptor. 5HT$_{1B}$ receptors are located post-synaptically in the cerebral region and on the peripheral sympathetic nerve-endings, the cerebral blood vessels and the trigeminal primary afferent nerves (G. J. Molderings, Naunyn-Schmiedeberg's Arch. Pharmacol., 1990. 342, 371; E. Hamel, Mol. Pharmacol., 1993, 44, 242 ; A. T. Bruinvels, Eur. J. Pharmacol., 1992, 227, 357). Their location implies that, by activation of 5HT$_{1B}$ receptor populations, it is possible to treat migraines and headaches with agonists by both a vascular and neurogenic effect. With antagonists it will be possible by action on the peripheral receptors to treat disorders of the cardiovascular system, such as unstable angina. In addition, the populations of 5HT$_{1B}$ receptors, which are also present in high concentrations in the cornu dorsale of the spinal cord, the basal ganglia, the hippocampus and the other limbic structures of the frontal cortex (C. Del Arco, Naunyn-Schmiedeberg's Arch. Pharmacol., 1992, 347, 248: S. Lowther, Eur. J. Pharmacol., 1992, 222, 137 ; X Langlois, J. Neurochem., 1995, 65. 2671), may be partly responsible for disorders of mood and behaviour and may be involved in the mechanisms of nociception. On the basis of their dual location, on the one hand on the post-synaptic serotoninergic neurons and on the other hand on cell bodies where they assume the role of autoreceptors, their involvement in pathogenesis can easily be deduced, and consequently selective ligands of those receptors may be used in the treatment of depression, anxiety, impulsive disorders and other psychiatric disorders associated with dysfunction of serotoninergic transmission (C. Waeber, *Neurochem. Res.,* 1990. 15, 567; K. Herrick-Davis, *J. Neurochem.,* 1988, 51, 1906).

Concerning the $5HT_{1B}$ (ex-$5HT_{1D\alpha}$) receptor, that receptor is predominant in the central nervous system of humans and guinea pigs. Furthermore, only $5HT_{1B}$ receptors are located as autoreceptors, which is not true of $5HT_{1D}$ (ex-$5HT_{1D\alpha}$) receptors. $5HT_{1B}/5HT_{1D}$ receptor ligands have been described in the Applications WO 96/00720 and WO 96/12713: they are naphthylpiperazine compounds. $5HT_{1B}/5HT_{1D}$ receptor antagonists having a biphenyl structure have also been described in the Application WO 96/19477. Those structures in no way suggest the compounds of the present invention. The Patent Application WO 95/07274 describes compounds used in the treatment of disorders of the central nervous system having a 4-aminopiperidine structure. In the general formula of the said compounds the extracyclic nitrogen is bonded by way of an alkane chain to benzodioxane, tetrahydronaphthalene and chroman nuclei. Those structures do not result in the structures of the present invention. The activity of the products of the present invention has been demonstrated in numerous biological and pharmacological tests, which are described in the pharmacological study found in Example 30 hereinbelow.

It was possible to evaluate in vitro the selectivity for $5HT_{1B}$ receptors by binding experiments, especially by comparison with $5HT_{1A}$ receptors.

Using the hypothermia test on the guinea-pig (M. Stingle et al., *J. of Pychopharmacology,* 1994. 8, 14) it was possible to determine the agonist or antagonist nature of the products of the invention.

The microdialysis experiments demonstrate the value of the products of the present invention in the treatment of various pathologies of the central nervous system. Carried out in the frontal cortex, these tests make it possible, in the case where the products cause an increase in the release of serotonin, to envisage their use for depression, impulsive disorders and obesity. If they cause a decrease in the release of serotonin they will be beneficial in the treatment of anxiety, panic attacks, sleep problems, cognitive problems and drug abuse problems. Finally, if they produce an increase in dopamine and/or noradrenalin, they will be beneficial in the treatment of schizophrenia and, as above, in the treatment of depression and cognitive problems.

The present invention relates also to pharmaceutical compositions comprising as active ingredient a compound of formula I or a physiologically tolerable salt thereof, mixed with or in association with one or more appropriate pharmaceutical excipients.

The pharmaceutical compositions so obtained are generally presented in dosage form containing from 0.5 to 25 mg of active ingredient. They may, for example, be in the form of tablets, dragees, gelatin capsules, suppositories or injectable or drinkable solutions, and may be administered by the oral, rectal or parenteral route, depending on the forms employed.

The dosage varies according to the age and weight of the patient, the administration route and associated treatments and ranges from 0.5 to 25 mg of active ingredient from 1 to 3 times per day.

The present invention relates also to a process for the preparation of compounds of formula I which is characterised in that:

a compound of formula II:

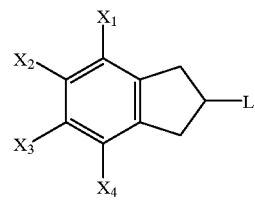

(II)

wherein $X_1$, $X_2$, $X_3$ and $X_4$ are as defined hereinbefore and L is a labile group such as

—$OSO_2CH_3$, —$OSO_2CF_3$,

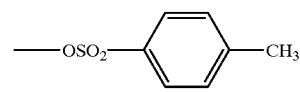

or a halogen atom selected from the atoms chlorine, bromine and iodine, is reacted with a compound of formula III:

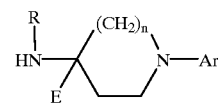

(III)

wherein R, E, n and Ar are as defined hereinbefore, the reaction being carried out more advantageously in a solvent, such as, for example, methyl isobutyl ketone, in the presence of an alkali metal carbonate, such as sodium or potassium carbonate, or in toluene in the presence of triethylamine;

or a compound of formula IV:

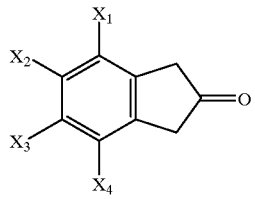

(IV)

wherein $X_1$, $X_2$, $X_3$ and $X_4$ are as defined hereinbefore is reacted with a compound of formula III defined above, in a reductive amination reaction, in the presence of sodium borohydride in tetrahydrofuran or sodium triacetoxyborohydride in dichloroethane, or
when E represents a hydrogen atom only, a compound of formula V:

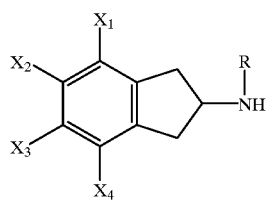
(V)

wherein $X_1$, $X_2$, $X_3$, $X_4$ and R are as defined hereinbefore is reacted with a compound of formula VI:

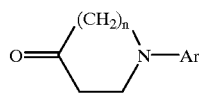
(VI)

wherein n and Ar are as defined hereinbefore,
in a reductive amination reaction, in the presence of sodium borohydride in tetrahydrofuran or sodium triacetoxyborohydride in dichloroethane,
to obtain a compound of formula I':

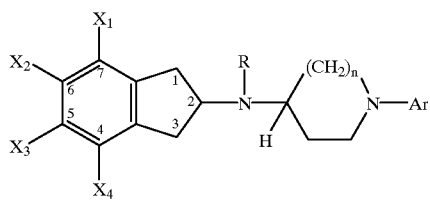
(I')

wherein $X_1$, $X_2$, $X_3$, $X_4$, R, Ar and n are as defined hereinbefore,
(I' being a sub-set of I),
or, finally,
when the group Ar represents

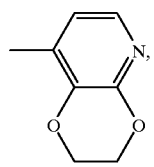

a compound of formula VII:

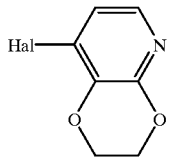
(VII)

wherein Hal represents a halogen atom selected from the atoms chlorine, bromine and iodine, is reacted with a compound of formula VIII:

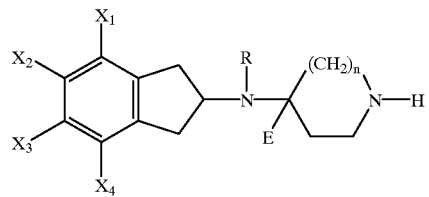
(VIII)

wherein $X_1$, $X_2$, $X_3$, $X_4$, R, E and n are as defined hereinbefore,
with the application of heat, in a solvent, such as, for example, pyridine, to obtain a compound of formula I":

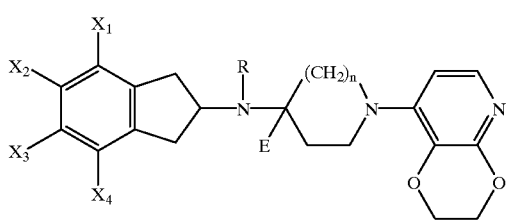
(I")

wherein $X_1$, $X_2$, $X_3$, $X_4$, R, E and n are as defined hereinbefore,
(I" being another sub-set of I);
and, when one or more of the substituents $X_1$, $X_2$, $X_3$ and $X_4$ represent(s) hydroxy, the compounds of formula I defined above in which one or more of the substituents $X_1$, $X_2$, $X_3$ and $X_4$ represent(s) a hydroxy radical may also be prepared from corresponding methoxy compounds which are treated with pyridine hydrochloride at 200° C.,
and furthermore, if desired, when the compounds of formula I contain one or more asymmetric carbon atoms, the optical isomers thereof are prepared according to conventional methods of resolution known from the literature.

The optical isomers may also be prepared starting from optically active starting materials.

The salts of compounds of formula I with pharmaceutically acceptable acids were obtained according to conventional methods as indicated in the Examples hereinbelow.

The starting materials are either known products or are products obtained from known substances according to known procedures, as described hereinbelow in Preparations 1 to 13.

The following Examples, given by way of non-limiting example, illustrate the present invention.

The melting points were determined using a Kofler hot plate (K), or a hot plate under a microscope (MK).

Synthesis of the Starting Materials

The starting materials used in the following Examples were prepared as follows:

Preparation 1

1-(2,3-dihydro[1,4]benzodioxin-5-yl)-4aminopiperidine

Step 1: 4-hydroxyiminotetrahydro-4H-pyran 40.6 g (0.406 mol) of tetrahydro-4H-pyran-4-one, 118.7 g (1.71 mol) of hydroxylamine hydrochloride and 118.1 g (1.44 mol) of sodium acetate in 810 ml of ethanol are mixed at room temperature and the mixture is heated at reflux for 20 hours and then allowed to cool. The solid is filtered off and rinsed with ethanol and then the filtrates are concentrated. The residue is taken up in 500 ml of ether and stirred vigorously for 2 hours (whitish, very viscous insoluble product). Insoluble material is removed by filtration and the filtrate is concentrated to yield 49.5 g of the desired product (theory: 46.7 g) containing 15% by weight of acetic acid (corrected yield:approximately 90%), which is used as it is.

Step 2: 4-aminotetrahydro-4H-pyran hydrochloride 49.3 g (≈0.405 mol) of the above compound are mixed with 15 ml of Raney nickel in 600 ml of ethanol and the mixture is then hydrogenated at room temperature under $5 \times 10^5$ Pa of hydrogen for 4 hours. After filtering off the Raney nickel, 200 ml of 4.1N ethereal hydrogen chloride (approximately 2 eq.) are added, then the solvents are evaporated off to yield 52.6 g of the desired product (theory: 55.7 g), which is used as it is.

Step 3: 1,5-dibromo-3-aminopentane hydrobromide 52.3 g (380 mmol) of the above compound are dissolved in 380 ml of fuming hydrobromic acid (60%) at room temperature, then the solution is heated at reflux for 24 hours. It is allowed to cool, then 500 ml of water are added: a solid appears after a few minutes. The whole is cooled in ice, then the solid is filtered off, rinsed with a very small amount of water, then made into a paste again in 200 ml of ether, filtered off, rinsed with ether and dried in vacuo over potassium hydroxide. In that manner, 69.5 g of the desired product (yield: 56%) are obtained in the form of a grey powder.

Step 4: Title Product 20 g (59.0 mmol) of the above compound are mixed with 8.9 g (58.9 mmol) of 5-amino-1,4-benzodioxane in 120 ml of chlorobenzene at room temperature, and the mixture is then heated at reflux overnight. It is allowed to cool the product is deposited on the walls of the three-necked flask. The chlorobenzene phase is decanted off, and then the residue is taken up in 50 ml of water then 200 ml of N hydrochloric acid, washed with ether (significant emulsion), rendered basic in the cold with concentrated sodium hydroxide solution and extracted 3 times with 200 ml of ethyl acetate each time. The combined organic phases are dried over magnesium sulphate, concentrated (15 g), then chromatographed on silica (eluant:dichloromethane/methanol/ammonium hydroxide, 95/5/0.5) to yield 4.7 g of the desired product (theory: 13.8 g) in the form of a paste.

Preparation 2

1-(2,3-dihydro[1,4]benzodioxin-5-yl)-4-methylaminopiperidine

Step 1: 1-(2,3-dihydro[1,4]benzodioxin-5-yl)-4-ethoxycarbonylaminopiperidine

At room temperature, 2.1 ml (14.9 mmol) of triethylamine are added in one go to 1.6 g (6.8 mmol) of the title compound of Preparation 1 in 20 ml of dichloromethane, and then, over a period of 30 minutes, 0.71 ml (7.5 mmol) of ethyl chloroformate is added dropwise thereto. The whole is stirred overnight at room temperature, then 100 ml of dichloromethane are added and the whole is washed with 100 ml of water, 100 ml of N hydrochloric acid (twice) and 100 ml of water. The organic phase is dried over magnesium sulphate and concentrated to yield 1.3 g of the desired product (yield: 65%).

Step 2: Title Product

At room temperature, 1.3 g (4.2 mmol) of the above compound in 13 ml of tetrahydrofuran are added dropwise over a period of 15 minutes to 0.32 g (8.5 mmol) of lithium aluminium hydride in 7 ml of tetrahydrofuran. The whole is heated at reflux for 1 hour 30 minutes, then left at room temperature overnight. The whole is hydrolysed in the cold with, in succession, 0.22 ml of water, 0.18 ml of 20% sodium hydroxide solution and 0.81 ml of water. After filtering off the salts and evaporating off the solvent, 0.77 g of the desired product is obtained (yield: 73%).

Preparation 3

1-(thiochroman-8-yl)-4-aminopiperidine

Step 1:

8-tert-butoxycarbonylaminothiochroman

At room temperature, 9.0 ml (64.4 mmol) of triethylamine, then 13.9 ml (64.4 mmol) of diphenylphosphoryl azide are added to 10 g (51.5 mmol) of thiochroman-8-carboxylic acid in 260 ml of toluene. The whole is heated at 90° C. for 2 hours, then 4.8 g (64.4 mmol) of tert-butanol dissolved in 10 ml of toluene are added dropwise and the temperature is subsequently maintained at 90° C. for a further 20 hours. The whole is allowed to cool and washed with 120 ml of water, 120 ml of 0.N hydrochloric acid, 120 ml of water, 120 ml of a saturated aqueous sodium hydrogen carbonate solution and 120 ml of water. After drying over magnesium sulphate and evaporation, the residue is taken up in cyclohexane and triturated, and a solid is removed by filtration; the filtrate is concentrated (13.3 g) and then chromatographed on 1 kg of silica (eluant: dichloromethane) to yield 11.2 g of the desired product (yield: 82%).

Step 2:

8-aminothiochroman 10 g (37.7 mmol) of the compound obtained in Step 1 above in 50 ml of dichloromethane are mixed with 50 ml of trifluoroacetic acid, and the mixture is stirred for 30 minutes at room temperature and then evaporated to dryness. The residue is taken up in ether and the solid obtained is filtered off and treated with N sodium hydroxide solution. The aqueous phase is extracted with ether and the ethereal phases are combined, dried over magnesium sulphate and concentrated to yield 4.48 g of the desired product (theory: 6.2 g).

Step 3: Title Product

By proceeding as described in Preparation 1 Step 4, 3.38 g of the desired product (yield: 49%) were obtained starting from 4.6 g (27.8 mmol) of the compound obtained in Step 2 above and 9.4 g (27.8 mmol) of 1,5-dibromo-3-aminopentane hydrobromide (described in Preparation 1 Step 3) in 60 ml of chlorobenzene.

Preparation 4:

1-(23-dihydro[1,4]benzoxathiin-5yl)piperid-4-one

Step 1: methyl 3-hydroxycyclohexylcarboxylate 30.4 g (0.2 mol) of methyl 3-hydroxybenzoate are reduced in accordance with the method described by F. Fache et al. (Tetrahedron Letters, 1995, 36 (6), p 885–888) to yield 14.6 g of the expected product (b.p./$_{133.28 Pa}$=90–95° C.).

Step 2:

3-methoxycarbonylcyclohexanone 14.4 g of the compound obtained in Step 1 are oxidised in accordance with the method described in J. Org. Chem., 1965, 30, 145–150 to yield 11.7 g of the expected product (b.p./$_{133.28\ Pa}$=80–85° C.), yield: 82%.

Step 3: 3-methoxycarbonylcyclohexanone ethylene mono-thioacetal 11.5 g (73.6 mmol) of the product obtained in Step 2, 10.3 g of 2-mercaptoethanol, 50 mg of para-toluenesulphonic acid and 10 ml of toluene are heated at reflux for 19 hours with azeotropic distillation. After evaporating off the solvent and excess 2-mercaptoethanol, the residue is distilled to yield 6.2 g of the expected product (b.p./$_{66.64\ Pa}$=100–10° C.).

Step 4: 5-methoxycarbonyl-2,3-dihydro[1,4]benzoxathiin 34.1 g (0.16 mol) of the product obtained in the above Step are treated in accordance with the method described by J. Y. Satah (J.Chem. Soc. Chem. Com., 1985, 1645–6) to yield, after flash chromatography twice on a silica column (eluant CH$_2$Cl$_2$), 1.7 g of the expected product.

Step 5: 2,3-dihydro[1,4]benzoxathiin-5-carboxylic acid 1.6 g of the compound obtained in Step 4 are treated for 2 hours at room temperature with 8 ml of 2N sodium hydroxide solution and 8 ml of methanol. After treatment, 1.3 g of the expected acid are isolated.

Step 6: tert-butyl N-(2,3-dihydro[1,4]benzoxathiin-5-yl)carbamate 1.25 g of the product obtained in the above Step, 1.12 ml of triethylamine, 1.73 ml of diphenylphosphoryl azide and 32 ml of toluene are mixed in a 100 ml two-necked flask, and the whole is heated at 90° C. for 3 hours. 1.2 ml of tert-butanol are then added dropwise over a period of 5 minutes and heating at 90° C. is continued for 20 hours. The mixture is allowed to cool, 70 ml of toluene are added, and the whole is washed twice with 50 ml of a 10% sodium carbonate solution and then with 50 ml of water. The whole is dried and evaporated to yield 1.7 g of the expected product.

Step 7: 5-amino-2,3-dihydro[1,4]benzoxathiin 1.5 g of the compound obtained in Step 6 are dissolved in ethyl acetate. The solution is cooled to 0° C. and then 5.5 g of gaseous HCl are introduced. The mixture is stirred for 24 hours and filtered over a frit to obtain 0.73 g of the hydrochloride of the expected product.

Step 8: 1-(2,3-dihydro[1,4]benzoxathiin-5-yl)piperid-4-ol 0.44 g of the free base obtained in Step 7 is mixed with 0.41 g of ω, ω'-dichloropentan-3-ol, 0.20 g of sodium iodide, 0.72 g of potassium carbonate and 1 ml of dimethylformamide and the whole is heated at reflux for 2 hours. The mixture is diluted with 50 ml of water and then extracted with ether, washed with brine and distilled water, dried and evaporated. Purification on silica yields 0.38 g of the expected product. Step 9: Title Product 0.35 g of the product of Step 8, 0.87 g of dicyclohexylcarbodiimide, 0.16 ml of pyridine, 4 ml of dimethyl sulphoxide and 7.5 ml of benzene are mixed at 5° C. 0.1 ml of trifluoroacetic acid is added dropwise and the whole is stirred at room temperature for 21 hours. Dilution is carried out with ethyl acetate, and insoluble material is filtered off. The filtrate is washed with water, dried, evaporated and purified on a silica column to yield 0.28 g of the expected title product.

Preparation 5

5-([1,2,4,]triazol-4-yl)indan-2-ylamine

Step 1: 5-nitro-2-(2-phthalimido)indan 3.1 g (17.2 mmol) of 5-nitroindan-2-ylamine are suspended in 23 ml of dimethyl-formamide. 2.75 g (18.6 mmol) of phthalic anhydride are added and the whole is heated at reflux for 10 minutes. After returning to room temperature, the reaction mixture is then poured into 500 ml of a mixture of water and ice to obtain the desired product (m.p. (MK): 195–199° C.).

Step 2: 5-amino-2-(2-phthalimido)indan 2 g (6.5 mmol) of the compound obtained in the above Step are suspended in 25 ml of methanol. 100 mg of platinum oxide are added and the whole is hydrogenated at room temperature under atmospheric pressure. Filtration of the catalyst and evaporation of the solvent yields 1.7 g of the expected product (m.p. (MK): 294–296° C.), yield: 94%.

Step 3: 5-([I,2,4]triazol-4-yl)-2-(2-phthalimido)indan 0.5 g (1.8 mmol) of the product obtained in Step 2 and 0.25 g (1.8 mmol) of N,N-dimethylformamide azine are heated at reflux for 17 hours in 14 ml of toluene in the presence of 17 mg of para-toluenesulphonic acid. The precipitate obtained is filtered off, rinsed with toluene and dried. 0.22 g of the expected product (m.p. (MK): 224–226° C.) is obtained, yield: 37%.

Step 4: Title Product 0.22 g (0.6 mmol) of the product obtained in Step 3 and 43 μl of hydrazine hydrate are introduced into 30 ml of ethanol. The whole is heated at reflux for 1 hour 30 minutes. After the addition of 100 ml of 1N HCl, the precipitate is filtered off and the filtrate is rendered alkaline with 1N sodium hydroxide solution. Extraction is carried out with methylene chloride to obtain 0.13 g of the expected product, yield: 100%.

Preparation 6

1-(2,3-dihydro[1,4]benzodioxin-5-yl)pyrrolidin-3-one

Step 1: 1-(2,3-dihydro[1,4]benzodioxin-5-yl)pyrrolidin-3-ol 10 g (66 mmol) of 5-amino-2,3-dihydro[1,4]benzodioxin, 7.65 ml of ω, ω'-dibromo-butan-2-ol and 18.25 g of K$_2$CO$_3$ in 125 ml of chlorobenzene are heated at reflux for 18 hours. After removal of the solvent by evaporation, the residue is taken up in methylene chloride and washed with water. Drying and evaporation yield 17.6 g of an oil which corresponds to the expected product.

Step 2: Title Product 0.51 ml of trifluoroacetic acid are added dropwise to a mixture composed of 2 g (9.04 mmol) of the product of Step 1, 5.6 g (27 mmol) of N,N-dicyclohexylcarbodiimide, 1.03 ml of pyridine, 25.8 ml of dimethyl sulphoxide and 48 ml of benzene while maintaining the temperature at 5° C. The reaction mixture is then stirred for 20 hours at room temperature. The mixture is diluted with ethyl acetate, insoluble material is filtered off, and the filtrate is washed with water, dried with MgSO$_4$ and evaporated to yield 2.5 g of product, which corresponds to the expected product.

Preparation 7

1-(chroman-8-yl)-4-aminopiperidine

Step 1: 1-(chroman-8-yl)piperid-4-one

Obtained starting from 8-aminochroman using the methods of operation of Steps 8 and 9 of Preparation 4.

Step 2: 1-(chroman-8-yl)-4-hydroxyiminopiperidine

A mixture composed of 1 g (4.32 mmol) of the product obtained in Step 1, 1.26 g of hydroxylamine hydrochloride, 1.26 g of sodium acetate and 20 ml of ethanol are heated at reflux for 1 hour. After removal of the solvent by evaporation, the residue is taken up in 100 ml of methylene chloride, washed with water, dried and evaporated to yield 0.9 g of the expected product.

Step 3: Title Product 0.9 g of the product obtained in Step 2 is hydrogenated at room temperature and atmospheric pressure in the presence of 1 ml of Raney nickel and1 ml of concentrated NH$_4$OH in 20 ml of ethanol. After 5 hours' contact, the catalyst is filtered off and the filtrate is evaporated to dryness. The residue is taken up in 100 ml of methylene chloride and extracted with 1N hydrochloric acid. The acid phase is rendered basic with concentrated sodium hydroxide solution and extracted with methylene chloride. After washing, drying and evaporation, 0.76 g of the expected product is isolated.

Preparation 8:

1-(2,3-dihydrobenzofuran-7-yl)-4-aminopiperidine

Obtained in the same manner as the product of Preparation 7, but using 7-amino-2,3-dihydrobenzofuran in Step 1.

Preparation 9

1-(benzofuran-7-yl)-4-aminopiperidine

Obtained in the same manner as the product of Preparation 7, but using 7-aminobenzofuran in Step 1.

Preparation 10

1-(6-fluorochroman-8-yl)piperid-4-one

Step 1: 6-fluorochroman-8-carboxaldehyde 13.74 g (90.28 mmol) of 6-fluorochroman are dissolved in 250 ml of methylene chloride. The whole is cooled to 0° C. and 20.15 ml of $TiCl_4$ are added dropwise. The solution becomes brown and is stirred for 10 minutes at room temperature. 8.78 ml (99.3 mmol) of α, α-dichloromethyl ether are then introduced. The whole is stirred overnight at room temperature, poured into ice-cold water and decanted. The organic phase is dried and evaporated to yield 17.7 g of a residue which is purified by chromatography on silica (eluant $CH_2Cl_2$/cyclohexane: 50/50). 6.3 g of the expected product are obtained. Yield: 38.7%. Step 2: 6-fluorochroman-8-carboxylic acid The aldehyde obtained in the above Step is dissolved in 52 ml of acetone. The solution is cooled to 0° C. 17.43 ml of Jones reagent are slowly added while maintaining the temperature below 10° C. The whole is stirred for 4 hours at room temperature, the acetone is evaporated off and the residue is taken up in 60 ml of water and extracted with ether. The ethereal phases are extracted with 1N sodium hydroxide solution. The basic phases are rendered acidic with concentrated hydrochloric acid and extracted with ether. 5.31 g of the expected product are obtained. Yield: 77.5%.

Step 3: Benzyl N-(6-fluorochroman-8-yl)carbamate

A solution composed of 137 ml of toluene, 5.3 g (27.07 mmol) of the acid obtained in the above Step, 4.72 ml of triethylamine and 7.29 ml (33.83 mmol) of diphenylphosphoryl azide are heated at 90° C. for 2 hours. While maintaining that temperature. 3.52 ml of benzyl alcohol are then added and the whole is left at the same temperature for 20 hours, washed with water, 0.5N hydrochloric acid, again with water and then with sodium hydrogen carbonate solution and finally with water. The whole is dried and evaporated to yield 8.2 g of the expected product.

Step 4: 8-amino-6-fluorochroman 8.1 g of the compound of Step 3 are dissolved in 80 ml of ethanol. The solution is hydrogenated at normal pressure and room temperature in the presence of 0.39 g of palladium-on-carbon. Filtration and evaporation yield 4.6 g of a liquid which corresponds to the expected product.

Step 5: Title Product 4.5 g of the compound obtained in the above Step are treated as described in Steps 8 and 9 of Preparation 4. 2.9 g of the expected product are obtained.

Preparation 11

1-(4-acetyloxychroman-8-yl)-4-aminopiperidine

Step 1: 4-acetyloxy-8-nitrochroman 5.7 g (29.2 mmol) of 4-hydroxy-8-nitrochroman are dissolved in 100 ml of methylene chloride. 5 ml of triethylamine are added and then 2.6 ml of acetyl chloride are slowly poured in. The reactants are left in contact for 1 hour 30 minutes and then 2 ml of triethylamine are added and 1 ml of acetyl chloride is slowly poured in. The whole is left for a further 1 hour at room temperature, diluted with methylene chloride, washed with water, with 1N hydrochloric acid and then with a 5% solution of sodium carbonate and finally with 100 ml of water. The whole is dried and evaporated to obtain 6.6 g of an orange oil, which corresponds to the expected product. Yield: 95%.

Step 2: 4-acetyloxy-8-aminochroman 6.6 g (27.8 mmol) of the product of Step 1 are dissolved in 85 ml of methanol. 0.43 g of platinum oxide is added and the whole is hydrogenated at room temperature and normal pressure for 4 hours. The catalyst is filtered off and rinsed and the filtrate is evaporated to yield 5.5 g of a viscous oil, which corresponds to the expected product. Yield: 96%.

Step 3: 1-(4-acetyloxychroman)piperid-4-one 7.5 g (30.7 mmol) of the base obtained in Step 2 are treated according to the methods of operation described in Steps 8 and 9 of Preparation 4. 0.4 g of the expected product is obtained.

Step 4: 1-(4-acetyloxychroman-8-yl)-4-hydroxyiminopiperidine 0.4 g of the compound obtained in the above Step is treated according to the method of operation described in Step 2 of Preparation 7 to yield 0.28 g of the expected product. Yield: 66%.

Step 5: Title Product 0.28 g of the compound of Step 4 is dissolved in a solution of 6 ml of ethanol and 0.3 ml of $NH_4OH$. 0.3 ml of Raney nickel is added and the whole is hydrogenated at room temperature under atmospheric pressure. After filtering off the catalyst, rinsing and evaporating, 0.25 g of the expected product is obtained. Yield: 96%.

Preparation 12

4-amino-1-(2,3dihydro[1,4]benzodioxin-5-yl)-4-methylpiperidine

Step 1: 1-(2,3-dihydro[1,4]benzodioxin-5-yl)-4-hydroxy-4-methylpiperidine 3.5 g (15 mmol) of 1-(2,3-dihydro[1,4]benzodioxin-5-yl)piperid-4-one are dissolved in 30 ml of ether. The solution is cooled to 0° C. and, while that temperature is maintained, 10 ml of a 3M methylmagnesium bromide solution in ether are added. The whole is stirred for 1 hour at that temperature and then for ½ hour at room temperature, hydrolysed by pouring into 100 ml of a saturated aqueous $NH_4Cl$ solution, and extracted with 100 ml of ether. The extract is dried and evaporated to yield a residue of 3.3 g, which is purified by flash chromatography on silica (eluant $CH_2Cl_2$/$CH_3COOC_2H_5$: 90/10). In that manner, 1.3 g of the expected product are isolated.

Step 2: 4-acetylamino-1-(2,3-dihydro[1,4]benzodioxin-5-yl)-4-methylpiperidine 1.03 g (4.1 mmol) of the product of Step 1 are dissolved in 4 ml of acetonitrile. 1 ml of concentrated $H_2SO_4$ is added dropwise over a period of 5 minutes while the temperature is maintained below 40° C. The whole is stirred overnight at room temperature and then poured into 50 ml of ice-cold 1N sodium hydroxide solution. The whole is extracted with methylene chloride, washed with water, dried and evaporated to yield 0.85 g of residue, which is purified by flash chromatography (eluants:methylene chloride/ethyl acetate: 50/50, then methylene chloride/methanol: 98/2). 0.54 g of the expected product is obtained.

Step 3: Title Product 0.51 g (1.76 mmol) of the product obtained in Step 2 is treated at reflux for one night with 3 ml of 3N HCl. 1 ml of concentrated HCl is added and the whole is heated at reflux for 24 hours, allowed to cool, rendered basic with 2N NaOH and extracted 3 times with 30 ml of CH₂Cl₂ each time. The organic phases are washed and then dried. 0.32 g of the expected product is obtained. Yield: 73%.

Preparation 13

6-aminocyclopenta [f][2,1,3]benzoxadiazole and its hydrochloride

Step 1: 2-acetylamino-5-amino-6-nitroindan 1.62 g of KNO₃ is introduced in portions into 2.85 g (15 mmol) of 2-acetylamino-5-aminoindan in 7.5 ml of concentrated H₂SO₄ that has been cooled to 0° C. The whole is stirred for 3 hours at 0° C. and then poured into ice-cold 6N sodium hydroxide solution, stirred, extracted with methylene chloride and then washed, dried and evaporated. 2.8 g of a black solid are isolated, which is purified on silica (eluant:methylene chloride/methanol: 97/3). In that manner, 1.46 g of the expected product are isolated. Yield: 42%.

Step 2: 6-acetylaminocyclopenta[f][2,1,3]benzoxadiazole

At 0° C., 0.46 g (6.6 mmol) of NaNO₂, and then 1.4 g (6 mmol) of the product of Step 1 dissolved in 10 ml of acetic acid, are added to 3 ml of sulphuric acid. After 15 minutes at 0° C., the mixture is poured onto 20 g of ice. The solution so obtained is poured dropwise into a vigorously stirred solution of 600 mg (9.2 mmol) of sodium azide in 12 ml of water. The whole is stirred for 10 minutes at room temperature and extracted 3 times with 40 ml of CH₂Cl₂ each time. The organic phases are washed with an aqueous 10% sodium carbonate solution, dried over MgSO₄ and filtered and 100 ml of dry toluene are added. The methylene chloride is evaporated off and the toluene solution so obtained is heated at reflux for 3 hours.

The whole is allowed to cool and the solid is filtered off, washed with toluene and dried in vacuo. The solid is then dissolved in 50 ml of ethanol and 5 ml of triethyl phosphite are added. The whole is heated at reflux for 1 hour 30 minutes and evaporated to isolate 0.91 g of the expected product.

Step 3: Title Product 0.87 g of the product obtained in Step 2 is dissolved in 10 ml of methanol. 5 ml of 6N HCl are added and the whole is heated at reflux for 24 hours. After evaporation, 0.88 g of the hydrochloride of the expected product is obtained.

EXAMPLE 1

1-(2,3-dihydro[1,4]benzodioxin-5-yl)-4-[N-(indan-2-yl)amino]piperidine and its dihydrochloride A mixture of 11 g (38 mmol) of indan-2-ol tosylate, 9 g (38 mmol) of the title compound of Preparation 1, 7.7 g (76 mmol) of triethylamine and 150 ml of toluene is heated at reflux for 24 hours. The mixture is evaporated to dryness, the residue is taken up in dichloromethane and 1N sodium hydroxide solution and decanted, and the organic phase is washed with water, dried over MgSO₄ and concentrated. The residue is purified by chromatography on silica (eluant: CH₂Cl₂/CH₃COOC₂H₅, 90/10). The product obtained, which corresponds to the expected structure, is converted into the dihydrochloride by the action of ethereal hydrogen chloride. Yield=15%. M.p.>260° C.

EXAMPLE 2

1-(2,3-dihydro[1,4]benzodioxin-5-yl)-4-[N-(indan-2-yl)-N-methylamino]pieridine and its fumarate 0.77 g (3.1 mmol) of 1-(2,3-dihydro[1,4]benzodioxin-5-yl)-4-methylaminopiperidine (described in Preparation 2), 0.89 g (3.1 mmol) of indan-2-ol tosylate, 1.3 g (9.3 mmol) of potassium carbonate and 32 ml of methyl isobutyl ketone are mixed at room temperature. The mixture is heated at reflux for 26 hours, with the addition of a further 0.2 g (0.7 mmol) of indan-2-ol tosylate after 1 hour 30 minutes, 3 hours 30 minutes, 6 hours 30 minutes and 22 hours. The whole is evaporated to dryness, and the residue is taken up in 100 ml of dichloromethane and washed 3 times with 100 ml of water each time. After drying over magnesium sulphate and concentration, the residue (1.3 g) is chromatographed on 130 g of silica (eluant:dichloromethane/ethyl acetate, 90/10, then dichloromethane/ethyl acetate/methanol, 90/10/1) to yield 0.16 g of the expected product in the form of a free base. The corresponding fumarate is obtained in ethanol by the addition of one equivalent of a 2% fumaric acid solution in ethanol. After filtration and drying, 0.11 g of the title product is obtained in the form of a solid having a melting point (MK) of 188–190° C. Yield=12%.

EXAMPLE 3

1-(2,3-dihydro[1,4]benzodioxin-5-yl)-4-[N-(5,6-methylenedioxyindan-2-yl)amino]-piperidine and its fumarate 1.0 g (4.3 mmol) of 1-(2,3-dihydro[1,4]benzodioxin-5-yl)-4-aminopiperidine (described in Preparation 1), 0.75 g (4.3 mmol) of 5,6-methylenedioxyindan-2-one and 2 g of 4 Åmolecular sieve in 16 ml of chloroform are stirred for one night at room temperature. The sieve is then filtered off and rinsed with a small amount of chloroform and the filtrate is concentrated. The residue is taken up in 16 ml of methanol and 4 ml of tetrahydrofuran, and 0.32 g (8.5 mmol) of sodium borohydride is added in one go; the whole is stirred overnight at room temperature and then evaporated to dryness. The residue is taken up in 100 ml of dichloromethane and washed twice with 50 ml of water each time. After drying over magnesium sulphate and concentration, the residue (1.66 g) is chromatographed on 160 g of silica (eluant:dichloromethane/methanol, 98/2) to yield 0.71 g of the expected product in the form of a free base.

The corresponding fumarate is obtained in ethanol by the addition of one equivalent of a 2% solution of fumaric acid in ethanol. After filtration and drying, 0.68 g of the expected fumarate having a melting point (MK) of 255–259° C. is obtained. Yield=31%.

EXAMPLE 4

4-[N-(indan-2-yl)amino]1-(thiochroman-8-yl) piperidine

Prepared in the same manner as the compound of Example 3 but using the compound of Preparation 3 instead of 4-amino-1-(2,3-dihydro[1,4]benzodioxin-5-yl)piperidine and indan-2-one instead of 5,6-methylenedioxyindan-2-one. After purification on silica (eluant: CH₂Cl₂/CH₃OH, 98/2), the expected product having a melting point (MK) of 109–112° C. obtained. Yield=8%.

EXAMPLE 5

1-(2,3-dihydro[1,4]benzodioxin-5-yl)-4-[N-(5,6-dimethoxyindan-2yl)amino]piperidine and its fumarate Prepared in the same manner as the compound of Example 3 but using 5,6-dimethoxy-indan-2-one instead of 5,6-methylenedioxyindan-2-one. Purification on silica using the same eluant yields the expected product, which is converted into the corresponding fumarate having a melting point (MK) of 212–216° C. Yield=12%.

EXAMPLE 6

1-(2,3-dihydro[1,4]benzodioxin-5-yl)4-[N-(5-methylindan-2-yl)amino]piperidine and its fumarate Prepared in the same manner as the compound of Example 3 but using 5-methylindan-2-one instead of 5,6-methylenedioxyindan-2-one. Purification employing the same conditions yields the expected product, the corresponding fumarate of which melts (MK) at 239–241° C. Yield=19%.

EXAMPLE 7

1-(2,3-dihydro[1,4]benzodioxin-5-yl)-4-[N-(-chloroindan-2-yl)amino]piperidine and its fumarate Prepared in the same manner as the compound of Example 3 but with replacement of the 5,6-methylenedioxyindan-2-one with 5-chloroindan-2-one. Purification on silica using the same eluant yields the expected product, the corresponding fumarate of which melts (MK) at 238–241° C. Yield=9%.

EXAMPLE 8

1-(2,3-dihydro[1,4]benzodioxin-5-yl)-4-[N-(5-methoxyindan-2-yl)amino]piperidine and its fumarate Prepared in the same manner as the compound of Example 3, but using 5-methoxyindan-2-one instead of 5,6-methylenedioxyindan-2-one. The fumarate of the expected product melts (MK) at 22214 227° C.

EXAMPLE 9

1-(2,3-dihydro[1,4]benzodioxin-5-yl)-4-[N-(5,6-dimethylindan-2-yl)amino]piperidine and its fumarate Prepared in the same manner as the compound of Example 3, but using 5,6-dimethyl-indan-2-one instead of 5,6-methylenedioxyindan-2-one. The fumarate of the expected product melts (MK) at 232–235° C.

EXAMPLE 10

1-(2,3-dihydro[1,4]benzodioxin-5-yl)-4-[N-(5-trifluoromethylindan-2-yl)-amino]piperidine and its fumarate Prepared in the same manner as the compound of Example 3, but using 5-trifluoromethyl-indan-2-one instead of 5,6-methylenedioxyindan-2-one. The fumarate of the expected product melts (MK) at 228–232° C.

EXAMPLE 11

1-(2,3-dihydro[1,4]benzodioxin-5-yl)-4-[N-(4,7-dimethoxyindan-2-yl)amino]piperidine and its hemifumarate Prepared in the same manner as the compound of Example 3, but using 4,7-dimethoxy-indan-2-one instead of 5,6-methylenedioxyindan-2-one. The hemifumarate of the expected product melts (MK) at 217–220° C.

EXAMPLE 12

1-(2,3-dihydro[1,4]benzodioxin-5-yl)4-[N-(5-fluoroindan-2-yl)amino]piperidine and its fumarate Prepared in the same manner as the compound of Example 3, but using 5-fluoroindan-2-one instead of 5,6-methylenedioxyindan-2-one. The fumarate of the expected product melts (MK) at 216–220° C.

EXAMPLE 13

4-[N-(indan-2-yl)-N-methylamino]-1-(2,3-dihydro-1,4-dioxino[2,3-b]pyridin-8-yl)-piperidine 1.1 g (6.5 mmol) of 8-chloro-2,3-dihydro-1,4-dioxino[2,3-b]pyridine, 3 g (13 mmol) of 4[N-(indan-2-yl)-N-methylamino]piperidine and 5 ml of pyridine are placed in a reactor. The whole is heated at 130° C. for 8 hours. After cooling, the whole is taken up in toluene and concentrated. The residue is chromatographed on 130 g of silica (eluant: $CH_2Cl_2/CH_3OH/NH_4OH$, 95/5/0.5) to yield the expected product which melts (MK) at 167–170° C. Yield=8.5%.

EXAMPLE 14

1-(2,3-dihydro[1,4]benzoxathiin-5-yl)-4-(indan-2-ylamino)piperidine and its hemifumarate 0.17 g (1 mmol) of indan-2-ylamine hydrochloride is introduced into 7 ml of 1,2-dichloroethane and then, in order, 0.14 ml (1.5 mmol) of triethylamine, 0.25 g of 1-(2,3-dihydro[1,4]benzoxathiin-5-yl)piperid-4-one (Preparation 4), 0.32 g (1.5 mmol) of sodium triacetoxyborohydride and 58 µl (1 mmol) of acetic acid are added. The whole is stirred for 20 hours at room temperature and then poured into 10 ml of 1N sodium hydroxide solution and extracted twice with 25 ml of ether each time. The combined organic phases are washed and dried. Evaporation yields 0.36 g of the title product, which is converted into the hemifumarate by the action of a 2% solution of fumaric acid in ethanol. In that manner, 0.27 g of hemifumarate is obtained. M.p. (MK)=220–223° C.

EXAMPLE 15

1-(chroman-8-yl)-4-(indan-2-ylamino)piperidine and its fumarate

Obtained in the same manner as the product of Example 14 but using 1-(chroman-8-yl)piperid-4-one instead of the product of Preparation 4. The corresponding fumarate melts (MK) at 236–240° C.

EXAMPLE 16

1-(2,3-dihydro[1,4]benzodioxin-5-yl)-3-(indan-2-ylamino)pyrrolidine and its dihydrochloride Obtained in the same manner as the product of Example 14 but using 1-(2,3-dihydro [1,4]benzodioxin-5-yl) pyrrolidin-3-one (Preparation 6) instead of the product of Preparation 4. The dihydrochloride of the title product prepared with a solution of ethereal hydrogen chloride melts (MK) at 245–248° C.

EXAMPLE 17

1-(6-fluorochroman-8-yl)-4-(indan-2-ylamino)piperidine and its fumarate

Obtained in the same manner as the product of Example 14 but using 1-(6-fluorochroman-8-yl)piperid-4-one (Preparation 10) instead of the product of Preparation 4. The fumarate of the expected product melts (MK) at 226–230° C.

EXAMPLE 18

1-(2,3-dihydro[1,4]benzodioxin-5-yl)-4-(5-nitroindan-2-ylamino)piperidine and its fumarate Obtained in the same manner as the product of Example 14 but using 5-nitroindan-2-ylamine hydrochloride instead of indan-2-ylamine hydrochloride and 1-(chroman-8-yl)piperid-4-one instead of the product of Preparation 4. The fumarate of the title product melts (MK) at 234–237° C.

EXAMPLE 19

1-(chroman-8-yl)-4-[5-(1,2,4-triazol-4-yl)indan-2-ylamino]piperidine and its hemifumarate Obtained in the same manner as the product of Example 14 but using 5-(1,2,4-triazol-4-yl)indan-2-ylamine hydrochloride (Preparation 5) instead of indan-2-ylamine hydrochloride and 1-(chroman-8-yl)piperid-4-one instead of the product of Preparation 4. The hemifumarate melts (MK) at 153–155° C.

EXAMPLE 20

1-(chroman-8-yl)-4-[(cyclopenta[f][2,1,3]benzoxadiazol-6-yl)amino]piperidine and its fumarate Obtained in the same manner as the product of Example 14 but using 6-aminocyclo-penta[f][2,1,3]benzoxadiazole hydrochloride (Preparation 13) instead of indan-2-ylamine hydrochloride and 1(chroman-8-yl)piperid-4-one instead of the product of Preparation 4. The fumarate of the title product melts (MK) at 225–227° C.

EXAMPLE 21

1-(chroman-8-yl)-4-[(5-fluoroindan-2-yl)amino]piperidine and its fumarate 0.49 g (3.27 mmol) of 5-fluoroindan-2-one and 0.76 g (3.27 mmol) of 1-(chroman-8-yl)-4-aminopiperidine (Preparation 7) in 25 ml of 1,2-dichloroethane are mixed together. 1.1 g of sodium triacetoxyborohydride and 0.19 ml of acetic acid are then introduced. The whole is stirred for 24 hours. The reaction mixture is poured into 1N sodium hydroxide solution and extracted with ether. The organic phases are washed, dried and evaporated. The residue is purified on a silica column (eluant $CH_2Cl_2/C_2H_5H$: 98/2).

0.64 g of a liquid is obtained the structure of which corresponds to the expected product, which is treated with a 2% solution of fumaric acid in ethanol. 0.67 g of the fumarate of the expected product is obtained. M.p. (MK): 227–231° C.

EXAMPLE 22

1-(2,3-dihydrobenzofuran-7-yl)4-[(5-fluoroindan-2-yl)amino]piperidine and its hemifumarate Obtained in the same manner as the product of Example 21 but using 1-(2,3-dihydro-benzofuran-7-yl)-4aminopiperidine (Preparation 8) instead of the product of Preparation 7. The hemifumarate of the expected product melts (MK) at 225–229° C.

EXAMPLE 23

1-(chroman-8-yl)-4-[(5,6-methylenedioxyindan-2-yl)amino]piperidine and its fumarate Obtained in the same manner as the product of Example 21 but using 5,6-methylene-dioxyindan-2-one instead of 5-fluoroindan-2-one. The fumarate of the expected product melts (MK) at 248–252° C.

EXAMPLE 24

1-(benzofuran-7-yl)-4-[(5-fluoroindan-2-yl)amino]piperidine and its hemifumarate Obtained in the same manner as the product of Example 21 but using 1-(benzofuran-7-yl)-4-aminopiperidine (Preparation 9) instead of the product of Preparation 7. The hemifumarate of the expected product melts (MK) at 219–222° C.

EXAMPLE 25

1-(chroman-8-yl)-4-[(5-methoxyindan-2-yl)amino]piperidine and its fumarate

Obtained in the same manner as the product of Example 21 but using 5-methoxyindan-2-one instead of 5-fluoroindan-2-one. The fumarate of the expected product melts (MK) at 218–223° C.

EXAMPLE 26

1-(4-hydroxychroman-8-yl)-4-(5,6-methylenedioxyindan-2-yl)amino]piperidine and its hemifumarate Step 1: 1-(4acetyloxychroman-8-yl)-4-[(5,6-methylenedioxyindan-2-yl)amino]piperidine Obtained in the same manner as the product of Example 21 but using 5,6-methylene-dioxyindan-2-one instead of 5-fluoroindan-2-one and 1-(4-acetyloxychroman-8-yl)-4-amino-piperidine (Preparation 11) instead of the product of Preparation 7. A yellow oil, which corresponds to the expected product, is isolated in a yield 26%.

Step 2: Title Product 100 mg (0.22 mmol) of the product obtained in Step 1 are dissolved in a solution of 2 ml of methanol and 1.5 ml of 1N sodium hydroxide solution. The reactants are left in contact for one night, then for one hour at 60° C. After returning to room temperature, the methanol is evaporated off, and the residue is diluted with water and extracted with methylene chloride. After drying and evaporation, 60 mg of a product which corresponds to the expected structure is isolated, which is converted into the fumarate by the action of a 2% solution of fumaric acid in ethanol. 0.44 g of a product that corresponds to the hemifumarate of the expected product is isolated. M.p.(MK): 252–253° C.

EXAMPLE 27

1-(2,3-dihydro[1,4]benzodioxin-5-yl)4-(indan-2-ylamino)-4-methylpiperidine and its fumarate Obtained in the same manner as the product of Example 21 but using indan-2-one instead of 5-fluoroindan-2-one and 4-amino-1(2,3-dihydro[1,4]benzodioxin-5-yl)-4-methylpiperidine (Preparation 12) instead of the product of Preparation 7. The fumarate of the expected product melts (MK) at 218–223° C.

EXAMPLE 28

1-(2,3-dihydro[(1,4]-benzodioxin-5-yl)-4-[N-(5-hydroxyindan-2-yl)amino]piperidine and its hemifumarate 1 g (2.2 mmol) of the dihydrochloride of the product of Example 8 and 0.77 g (6.6 mmol) of pyridine hydrochloride are mixed and heated at 200° C. for 1 hour. The whole is allowed to return to room temperature and taken up in 100 ml of methylene chloride and 100 ml of a dilute solution of ammonium hydroxide. The phases are separated, the organic phase is dried and the solvent is evaporated off. 0.78 g of the expected product is obtained which is converted into 0.61 g of the corresponding hemifumarate. M.p. (MK): 250–260° C.

EXAMPLE 29

1-(chroman-8-yl)-4-[N-(5-hydroxyindan-2-yl)amino] piperidine and its hemifumarate The procedure is the same as that in Example 28 except that the product of Example 25 is used instead of the product of Example 8. The hemifumarate of the expected product melts (MK) above 350° C.

EXAMPLE 30

Pharmacological Study

Binding Studies

5-$HT_{1B}$ Binding a) Preparation of the Membranes

After the dissection of guinea-pig brains, the extracted striata are frozen and then homogenised in 20 volumes (weight/volume) of 50 mM tris-HCl (pH 7.7 at room temperature) containing 4 mM $CaCl_2$ and 0.1% ascorbic acid, and centrifuged at 48,000 g for 25 minutes at 4° C. The supernatant is separated and the precipitate is resuspended in the same volume of buffer before being incubated at 37° C. for 15 minutes in order to extract the endogenous serotonin. Finally, the suspension is centrifuged at 48,000 g for 25 minutes at 4° C. and the precipitate is resuspended in 80 volumes of buffer that contains 10 µM pargyline.

b) Binding Study

The binding studies ([$^3$H]-GR 125743) are carried out in triplicate in the following buffer: 50 mM tris-HCl (pH 7.7 at room temperature) containing 4 mM $CaCl_2$, 0.1% ascorbic acid and 10 µM pargyline. The final volume of 500 µl is formed by 100 µl of radioligand, 100 µl of buffer or compound to be tested and 300 µl of membranes. The serotonin (10 µM) is used to define the non-specific binding. In the competition experiments, the concentration of [$^3$H]-GR 125743 is 1 nM. The incubations are started by the addition of the membrane preparation and continue for 60 minutes at room temperature. The reaction is stopped by rapid filtration across Whatman GF/B filters pretreated with 0.1% polyethyleneimine, followed by three rinses with cold buffer. The specific binding represents approximately 90% of the total binding at concentrations of radioligand approaching the Kd value.

Analysis of the Data

The data are analysed by non-linear regression using the PRISM programme (Graphpad Software Inc., San Diego, Calif.) in order to determine the Kd values (dissocation constant of the radioligand), the Bmax values (maximum number of sites) for the saturation experiments and the $IC_{50}$ values (50% inhibiting concentration) and the Hill number for the competition experiments. The inhibition constant ($K_i$) is calculated according to the Cheng-Prussof equation: $K_i=IC_{50}/1+_{L/Kd}$ wherein L represents the concentration of the radioligand. The results are expressed as $pK_i=-\log K_i$.

The compounds of the present invention demonstrate a very good affinity for the $5HT_{1B}$ receptor. By way of example, the $pK_i$ of the compound of Example 3 is 8.5.

5$HT_{1A}$ Binding

The 5$HT_{1A}$ receptor binding studies were carried out according to methods known and described in the literature (cf. S. J. Peroutka, *J. Neurochem.*, 1986, 47, 529–40, M. J. Millan, *J. Pharmacol. Exp. Ther.*, 1994, 268, 337–52). The results are also expressed as $pK_i$. The compounds of the present invention have a very low affinity for the 5$HT_{1A}$ receptor. By way of example the $pK_i$ of the compound of Example 3 is 6.2.

This demonstrates the excellent selectivity of the products of the invention.

Hypothermia Test in the Guinea-Pig

The guinea-pigs are kept in batteries of three, with free access to food and water, for one week before entering the study. One hour before each experiment, the guinea-pigs are placed in individual cages with free access to water. They are put back in their respective batteries at the end of each experiment. The temperature measurements are carried out using a digital thermometer and a rectal probe. Each guinea-pig is weighed, its base body temperature is taken and then the compound of the present invention to be evaluated is injected i.p. or p.o. In the case of an agonist, the body temperature of each guinea-pig is taken every 30 minutes for 2 hours.

In the case of an antagonist, 15 minutes after its injection each guinea-pig is injected again i.p. with the prototype agonist 5$HT_{1B}$: GR46611 (5 mg/kg). The temperature is then taken every 30 minutes for 2 hours.

The criterion used for evaluation is the difference in temperature at a given time in relation to the base temperature. For each dose of product and for each time ($t_{30}$, $t_{60}$, $t_{90}$, $t_{120}$) the mean and the standard error of the mean are calculated.

By way of example, and to illustrate the effects of the products of the invention at $t_{90}$ and by the i.p. route, the results of the compound of Example 1, which acts as an antagonist, are listed in the following Table.

| Injection 1 (a) | Injection 2 (a) | ΔT° C. (b) (at 90 minutes) |
|---|---|---|
| Vehicle | Vehicle | 0 ± 0.1 |
| Vehicle | GR 46611 5 mg/kg | −1.04 ± 0.15 |
| Product of Example 1 0.04 mg/kg | GR 46611 5 mg/kg | −0.82 ± 0.30 |
| Product of Example 1 0.16 mg/kg | GR 46611 5 mg/kg | −0.75 ± 0.22 |
| Product of Example 1 0.63 mg/kg | GR 46611 5 mg/kg | −0.15* ± 0.10 |

(a): administration route i.p.
(b): the values are the means ± s.e.m. N ≧ 6 per value
\*: P < 0.05 versus vehicle/GR 46611 according to the Dunnett test Microdialysis Experiment in Rats The rats are anaesthetised with pentobarbital (60 mg/kg i.p.). They are placed in a Kopf stereotaxic apparatus and the cannula guide is implanted in the frontal cortex cingulum in accordance with the coordinates described as follows in the Paxinos and Watson atlas (1982): AP:+2.2, L:±0.6, DV:−0.2. The rats are placed in separate cages and are not used in dialysis until 5 days later. On the day of dialysis, the probe is slowly inserted and maintained in its position. The probe is perfused at a rate of flow of 1 µl/min. with a solution of 147.2 mM NaCl, 4 mM KCl and 2.3 mM $CaCl_2$ adjusted to pH 7.3 with a phosphate buffer (0.1M). Two hours after implantation, samples are collected every 20 minutes for 4 hours. Three base samples are collected before the administration of the products to be tested. The rats are left in their individual cages for the entire experiment. At the end of the experiment the rats are decapitated and the removed brain is frozen in isopentane. Sections 100 µm thick are cut and coloured with cresyl violet, allowing verification of the location of the probes. Simultaneous quantification of dopamine, norepinephrine and serotonin is carried out as follows: 20 µl of dialysis samples are diluted with 20 µl of mobile phase ($NaH_2PO_4$: 75 mM, EDTA: 20 µM, sodium 1-decanesulphonate: 1 mM, methanol: 17.5%, triethylamine: 0.01%, pH: 5.70) and 33 µl are analysed by HPLC with an inverse phase column (Hypersil ODS 5 µm, C18, 150×4.6 mm, Thermo Separation Products, Les Ulis, France) thermostatically controlled at 45° C. and quantified by way of a coulometric detector. The potential of the first electrode of the detector is fixed at −90 mV (reduction) and the second at +280 mV (oxidation). The mobile phase is injected with a Beckman 116 pump at a rate of flow of 2 ml/min. The sensitivity limits for dopamine, norepinephrine and serotonin are 0.55 fmol per sample. All of the products of the invention are injected by the subcutaneous route in a volume of 1.0 ml/kg. The products are dissolved in distilled water to which a few drops of lactic acid are added if necessary.

In the case of the agonists a decrease in the extracellular concentration of serotonin was observed (see Table below).

In the case of the antagonists, reversion of the decrease in the extracellular concentration of serotonin produced by the agonist GR46611 injected 20 minutes after the compounds of the invention to be tested was observed (see Table below).

| Vehicle + Vehicle | Vehicle + GR 46611 (10.0 mg/kg, s.c.) | Product of Example 1 (10.0 mg/kg, s.c.) + Vehicle | Product of Example 1 (10.0 mg/kg, s.c.) + GR 46611 (10.0 mg/kg, s.c.) |
|---|---|---|---|
| M ± s.e.m (n) | M ± s.e.m (n) | M ± s.e.m. (n) | M ± s.e.m. (n) |
| +2.0 ± 2.5 (10) | −40.7 ± 2.3 (5) | −9.5 ± 3.7 (8) | +0.7 ± 3.4 (6) |

M±s.e.m.=mean of the effect all times merged after administration of the products±standard error of the mean, and n=number of animals. The quantities of the neurotransmitters are expressed as a function of the mean of the three base values before administration of the products and are defined as 0%. The base level corresponds to 0.59±0.08 pg/20 μl of microdialysate, n=10. The reversion of the decrease of the extracellular concentration of serotonin produced by GR 46611 is evaluated statistically by an analysis of variance with drugs as between factor, $F(1,25) = 26.5$, $P<0.01$.

We claim:

1. A compound selected from:

those of formula I:

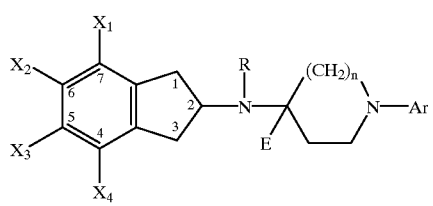

(I)

wherein:

n represents 1 or 2;

- Ar represents:

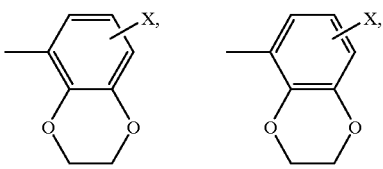

(X being a hydrogen or flourine atom)

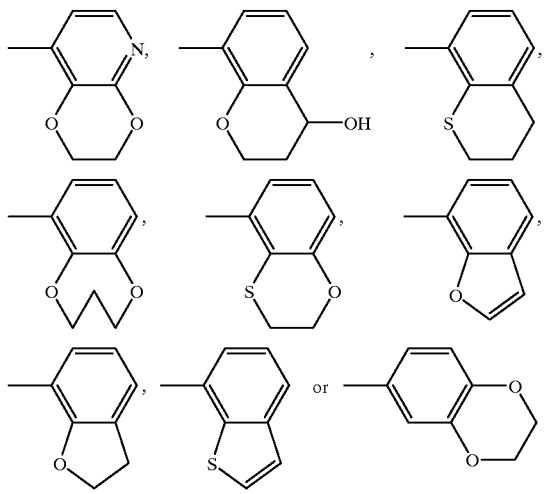

R represents hydrogen, linear or branched $(C_1-C_5)$-alkyl, or aralkyl,

E represents hydrogen or methyl, and $X_1$, $X_2$, $X_3$ and $X_4$, which may be identical or different, each represents hydrogen or halogen, straight-chain or branched $(C_1-C_5)$-alkyl or $(C_1-C_5)$-alkoxy, trifluoromethyl, hydroxy, cyano, or nitro, or

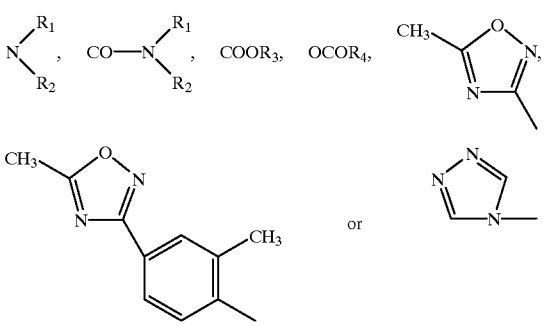

wherein: $R_1$, $R_2$ and $R_3$, which may be identical or different, each represents hydrogen or straight-chain or branched $(C_1-C_5)$-alkyl, and $R_4$ represents straight-chain or branched $(C_1-C_5)$-alkyl, and/or a pair adjacent to one another form, together with the carbon atoms of the phenyl nucleus to which they are bonded, a 5-membered or 6-membered ring consisting of atoms selected from carbon, oxygen, nitrogen and sulphur, where they exist in the form of a racemic mixture or in the form of optical isomers, and physiologically-tolerable acid addition salts thereof.

2. A compound of claim 1 selected from the group consisting of:

1-(2,3-dihydro[1,4]benzodioxin-5-yl)-4-[N-(indan-2-yl)amino]piperidine and its dihydrochloride, 1-(2,3-dihydro[1,4]benzodioxin-5-yl)-4-[N-(indan-2-yl)-N-methylamino]piperidine and its fumarate, 1-(2,3-dihydro[1,4]benzodioxin-5-yl)-4-[N-(5,6-methylenedioxyindan-2-yl)amino]piperidine and its fumarate, 4-[N-(indan-2-yl)amino]-1-(thiochroman-8-yl)piperidine, 1-(2,3-dihydro[1,4]benzodioxin-5-yl)-4-[N-(5,6-dimethoxyindan-2-yl)amino]piperidine and its fumarate, 1-(2,3-dihydro[1,4]benzodioxin-5-yl)-4-[N-(5-methylindan-2-yl)amino]piperidine and its fumarate,
1-(2,3-dihydro[1,4]benzodioxin-5-yl)-4-[N-(5-chloroindan-2-yl)amino]piperidine and its fumarate,
1-(2,3-dihydro[1,4]benzodioxin-5-yl)-4-[N-(5'-methoxyindan-2-yl)amino]piperidine and its fumarate,
1-(2,3-dihydro[1,4]benzodioxin-5-yl)-4-[N-(5,6-dimethylindan-2-yl)amino]piperidine and its fumarate,
1-(2,3-dihydro[1,4]benzodioxin-5-yl)-4-[N-(5-trifluoromethylindan-2-yl)-amino]piperidine and its fumarate,
1-(2,3-dihydro[1,4]benzodioxin-5-yl)-4-[N-(4,7-dimethoxyindan-2-yl)amino]piperidine and its hemifumarate,
1-(2,3-dihydro[1,4]benzodioxin-5-yl)-4-[N-(5-fluoroindan-2-yl)amino]piperidine and its fumarate,
4-[N-(indan-2-yl)-N-methylamino]-1-(2,3-dihydro-1,4-dioxino[2,3-b]pyridin-8-yl)piperidine,
1-(2,3-dihydro[1,4]benzoxathiin-5-yl)-4-(indan-2-ylamino) piperidine and its hemifumarate,
1-(chroman-8-yl)-4-(indan-2-yl amino)piperidine and its fumarate,
1-(2,3-dihydro[1,4]benzodioxin-5-yl)-3-(indan-2-ylamino) pyrrolidine and its dihydrochloride,
1-(6-fluorochroman-8-yl)-4-(indan-2-ylamino)piperidine and its fumarate,
1-(2,3-dihydro[1,4]benzodioxin-5-yl)-4-(5-nitroindan-2-ylamino)piperidine and its fumarate,
1-(chroman-8-yl)-4-[5-(1,2,4-triazol-4-yl)indan-2-ylamino] piperidine and its hemifumarate,
1-(chroman-8-yl)-4-[(cyclopenta[f][2,1,3]benzoxadiazol-6-yl)amino]piperidine and its fumarate,
1-(chroman-8-yl)-4-[(5-fluoroindan-2-yl)amino]piperidine and its fumarate,
1-(2,3-dihydrobenzofuran-7-yl)-4-[(5-fluoroindan-2-yl) amino]piperidine and its hemifumarate,
1-(chroman-8-yl)-4-[(5,6-methylenedioxyindan-2-yl) amino]piperidine and its fumarate,
1-(benzofuran-7-yl)-4-[(5-fluoroindan-2-yl)amino] piperidine and its hemifumarate,
1-(chroman-8-yl)-4-[(5-methoxyindan-2-yl)amino] piperidine and its fumarate,
1-(4-hydroxychroman-8-yl)-4-[(5,6-methylenedioxyindan-2-yl)amino]piperidine and its hemifumarate,
1-(2,3-dihydro[1,4]benzodioxin-5-yl)-4-(indan-2-ylamino)-4-methylpiperidine and its fumarate,
1-(2,3-dihydro[1,4]-benzodioxin-5-yl)-4-[N-(5-hydroxyindan-2-yl)amino]piperidine and its hemifumarate, and
1-(chroman-8-yl)-4-[N-(5-hydroxyindan-2-yl)amino] piperidine and its hemifumarate.

3. A compound according to claim 1 which is 1-(2,3-dihydro[1,4]benzodioxin-5-yl)-4-[N-(indan-2-yl)amino] piperidine or its dihydrochloride.

4. A compound according to claim 1 which is 1-(2,3-dihydro[1,4]benzodioxin-5-yl)-4-[N-(5,6-methylenedioxyindan-2-yl)amino]piperidine or its fumarate.

5. A compound according to claim 1 which is 1-(2,3-dihydro[1,4]benzodioxin-5-yl)-4-[N-(5-fluoroindan-2-yl) amino]piperidine or its fumarate.

6. A compound according to claim 1 which is 1-(chroman-8-yl)-4-(indan-2-ylamino)piperidine or its fumarate.

7. A compound according to claim 1 which is 1-(2,3-dihydro[1,4]benzodioxin-5-yl)-4-[N-(5-hydroxyindan-2-yl) amino]piperidine or its hemifumarate.

8. A method for treating a living animal body afflicted with a condition selected from depression, anxiety, impulsive disorders, obesity or a psychotic disorder associated with dysfunction of serotoninergic transmission, comprising the step of administering to the said living animal body a $5HT_{1B}$ antagonistic effective amount of a compound of claim 1, which is effective for the alleviation of said condition.

9. A pharmaceutical composition having selective binding affinity for $5HT_{1B}$ receptors, comprising as active ingredient a $5HT_{1B}$ antagonistic effective amount of a compound according to claim 1, together with one or more pharmaceutically-appropriate excipients.

10. A method for treating a living animal body afflicted with a condition selected from depression, anxiety, impulsive disorders, obesity, or a psychotic disorder associated with dysfunction of serotoninergic transmission, comprising the step of administering to the said living animal body a $5HT_{1B}$ antagonistic effective amount of a compound of claim 2, which is effective for the alleviation of said condition.

11. A pharmaceutical composition having selective binding affinity for $5HT_{1B}$ receptors, comprising as active ingredient a $5HT_{1B}$ antagonistic effective amount of a compound according to claim 2, together with one or more pharmaceutically-appropriate excipients.

12. A method for treating a living animal body afflicted with a condition selected from depression, anxiety, impulsive disorders, obesity, or a psychotic disorder associated with dysfunction of serotoninergic transmission, comprising the step of administering to the said living animal body a $5HT_{1B}$ antagonistic effective amount of a compound of claim 3, which is effective for the alleviation of said condition.

13. A method for treating a living animal body afflicted with a condition selected from depression, anxiety, impulsive disorders, obesity, or a psychotic disorder associated with dysfunction of serotoninergic transmission, comprising the step of administering to the said living animal body a $5HT_{1B}$ antagonistic effective amount of a compound of claim 4, which is effective for the alleviation of said condition.

14. A method for treating a living animal body afflicted with a condition selected from depression, anxiety, impulsive disorders, obesity, or a psychotic disorder associated with dysfunction of serotoninergic transmission, comprising the step of administering to the said living animal body a $5HT_{1B}$ antagonistic effective amount of a compound of claim 5, which is effective for the alleviation of said condition.

15. A method for treating a living animal body afflicted with a condition selected from depression, anxiety, impulsive disorders, obesity, or a psychotic disorder associated with dysfunction of serotoninergic transmission, comprising the step of administering to the said living animal body a $5HT_{1B}$ antagonistic effective amount of a compound of claim 6, which is effective for the alleviation of said condition.

16. A method for treating a living animal body afflicted with a condition selected from depression, anxiety, impulsive disorders, obesity, or a psychotic disorder associated with dysfunction of serotoninergic transmission, comprising the step of administering to the said living animal body a $5HT_{1B}$ antagonistic effective amount of a compound of claim 7, which is effective for the alleviation of said condition.

17. A pharmaceutical composition having selective binding affinity for $5HT_{1B}$ receptors, comprising as active ingredient a $5HT_{1B}$ antagonistic effective amount of a compound according to claim 3, together with one or more pharmaceutically-appropriate excipients.

18. A pharmaceutical composition having selective binding affinity for $5HT_{1B}$ receptors, comprising as active ingredient a $5HT_{1B}$ antagonistic effective amount of a compound according to claim 4, together with one or more pharmaceutically-appropriate excipients.

19. A pharmaceutical composition having selective binding affinity for $5HT_{1B}$ receptors, comprising as active ingredient a $5HT_{1B}$ antagonistic effective amount of a compound according to claim 5, together with one or more pharmaceutically-appropriate excipients.

20. A pharmaceutical composition having selective binding affinity for $5HT_{1B}$ receptors, comprising as active ingredient a $5HT_{1B}$ antagonistic effective amount of a compound according to claim 6, together with one or more pharmaceutically-appropriate excipients.

21. A pharmaceutical composition having selective binding affinity for $5HT_{1B}$ receptors, comprising as active ingredient a $5HT_{1B}$ antagonistic effective amount of a compound according to claim 7, together with one or more pharmaceutically-appropriate excipients.

* * * * *

UNITED STATES PATENT AND TRADEMARK OFFICE
CERTIFICATE OF CORRECTION

PATENT NO. : 5,968,954
DATED : Oct. 19, 1999          Page 1 of 2
INVENTOR(S) : J.L. Peglion, B. Goument, M. Millan, A. Gobert It is certified that error appears in the above-indentified patent and that said Letters Patent is hereby corrected as shown below:

Column 3, line 11:  "(ex-5HT$_{1D\alpha}$) receptor," should read
    -- (ex-5HT$_{1D\beta}$) receptor, --.

Column 7, line 32:  Insert -- : -- after the word "cool".

Column 8, line 18:  "0.N" should read -- 0.1N --.

Column 8, line 47:  "1-(23-" should read -- 1-(2,3- --.

Column 9, line 3:  "100-10°" at the end of the line
    should read -- 100-110° --.

Column 9, line 43:  "Step 9: Title Product" should begin
    a new paragraph.

Column 9, line 55:  "5-([1,2,4,]" should read
    -- 5-([1,2,4] --.

Column 11, line 25:  "Step 2: 6-fluorochroman....."
    should begin a new paragraph.

Column 15, line 15:  At the end of the line, "[N-(-"
    should read -- [N-(5- --.

Column 15, line 32 (approx.):  "22214 227°" should read
    -- 222-227° C. --.

Column 17, line 38:  "(eluant $CH_2Cl_2$ /$C_2H_5H$: 98/2)."
    should read -- (eluant $CH_2Cl_2$ /$C_2H_5OH$: 98/2)."

UNITED STATES PATENT AND TRADEMARK OFFICE
CERTIFICATE OF CORRECTION

PATENT NO. : 5,968,954
DATED : Oct. 19, 1999
INVENTOR(S) : J.L. Peglion, B. Goument, M. Millan, A. Gobert It is certified that error appears in the above-indentified patent and that said Letters Patent is hereby corrected as shown below:

Column 17, line 51: At the beginning of the line, insert a -- -(hyphen) -- after "4".

Column 18, line 16 (approx.): At the end of the line, "-4-(5,6-" should read: -- -4-[(5,6- --.

Column 19, line 52: "$K_i = IC_{50}/1+_{L/Kd}$" should read -- $K_i = IC_{50}/1+L_{/Kd}$ --.

Column 23, line 5: At the end of the line, "[N-(5'-" should read -- [N-(5-" --.

Signed and Sealed this

Eleventh Day of April, 2000

*Attest:*

Q. TODD DICKINSON

*Attesting Officer*     *Director of Patents and Trademarks*